United States Patent
Weismann et al.

[11] Patent Number: 5,647,351
[45] Date of Patent: Jul. 15, 1997

[54] VENTILATING SYSTEM FOR SUPPLYING A PATIENT WITH RESPIRATORY GAS AND METHOD FOR TRIGGERING THE RESPIRATORY PHASES IN SAID SYSTEM

[75] Inventors: Dieter Weismann, Gross Grönau, Germany; Gregory-Alan Colla, North Sydney, Australia; Dirk Fiebelkron, Lübeck, Germany

[73] Assignee: Dragerwerk AG, Lübeck, Germany

[21] Appl. No.: 524,535

[22] Filed: Sep. 7, 1995

[30] Foreign Application Priority Data

Sep. 10, 1994 [DE] Germany ............... 44 32 219.4

[51] Int. Cl.⁶ ................................................. A61M 16/00
[52] U.S. Cl. ........................... 128/204.21; 128/204.23; 128/204.26
[58] Field of Search ...................... 128/204.18, 204.21, 128/204.23, 204.26

[56] References Cited

U.S. PATENT DOCUMENTS

| | | | |
|---|---|---|---|
| 4,036,221 | 7/1977 | Hillsman | 128/204.23 |
| 4,957,107 | 9/1990 | Sipin | 128/204.21 |
| 5,048,515 | 9/1991 | Sanso | 128/204.18 |
| 5,107,831 | 4/1992 | Halpern et al. | 128/204.23 |
| 5,161,525 | 11/1992 | Kimm et al. | 128/204.23 |
| 5,313,937 | 5/1994 | Zdrojkowski | 128/204.23 |
| 5,433,193 | 7/1995 | Sanders et al. | 128/204.23 |

*Primary Examiner*—Aaron J. Lewis
*Attorney, Agent, or Firm*—Walter Ottesen

[57] ABSTRACT

A ventilating system for supplying a patient with respiratory gas has an apparatus for measuring a respiratory gas flow curve 27 and a respiratory gas pressure curve 28 and has an evaluation circuit 8 for processing at least the respiratory gas flow curve and switching over the respiratory phases. As switchover values from one respiratory phase to the other, the evaluation circuit 8 utilizes predetermined trigger thresholds $T_{IL}$, $T_{EL}$ of the respiratory gas flow curve 27. The ventilating system is improved in such a manner that a good adaptation thereof to the breathing effort of the patient 2 is provided even when leakage is present. This task is solved in that, in the evaluation circuit, the respiratory gas flow curve 27 and the respiratory gas pressure curve 28 are logically coupled during both the inspiratory phase and the expiratory phase. This logic operation takes place in accordance with a predetermined function. From the foregoing, an inspiratory trigger ancillary threshold $Z_I$ and an expiratory trigger ancillary threshold $Z_E$ are computed as an additional switchover criterion. These trigger ancillary thresholds $Z_I$ and $Z_E$ are added to the trigger thresholds $T_{IL}$ and $T_{EL}$, respectively. A method for triggering the respiratory phase in the system is also disclosed.

4 Claims, 3 Drawing Sheets

VENTILATING SYSTEM FOR SUPPLYING A PATIENT WITH RESPIRATORY GAS AND METHOD FOR TRIGGERING THE RESPIRATORY PHASES IN SAID SYSTEM

FIELD OF THE INVENTION

The invention relates to a ventilating system for supplying a patient with respiratory gas and includes a device for measuring a curve of respiratory gas flow and a curve of respiratory gas pressure. The system further includes an evaluation circuit which switches between respiratory phases and processes at least the curve of respiratory gas flow. The evaluation circuit utilizes predetermined trigger thresholds of the respiratory gas flow curve as values for switchover from one respiratory phase to the other. The invention also relates to a method for triggering the respiratory phases in said system.

BACKGROUND OF THE INVENTION

U.S. Pat. No. 5,303,700 discloses a method for detecting the respiratory phases of a patient and for controlling a ventilating apparatus with trigger thresholds obtained from the respiratory gas flow curve. In the ventilating apparatus disclosed in this patent, a significant increase of the steepness of the respiratory gas flow curve between respective zero crossovers of the respiratory gas flow is used as a trigger threshold.

It is also known to utilize the drop of the respiratory gas flow to 25% of the maximum value as a trigger criterion for the switchover from inspiration to expiration. The respiratory gas pressure is measured synchronously to the respiratory gas flow and evaluated.

Problems with respect to the switchover between the respiratory phases can occur when there is leakage, for example, leakages within the system because a mask is not seated sufficiently tight or because of an unblocked tube or even because of leakages caused by a fistula in the patient. The above-mentioned switchover is referred to specific function values of the respiratory gas flow curve.

In a pressure-controlled ventilating operation, a compensating flow is metered during expiration and during inspiration to compensate for leakages of this kind. In this way, the respiratory pressure can be maintained at the preselected value. A leakage compensation of this kind is disclosed, for example, in the German publication entitled "Evita 2, Das universelle Beatmungsgerät für die Intensivtherapie" published by Drägerwerk Aktiengesellschaft as publication no. 9048262, pages 14 and 15. However, by metering the compensating flow, the zero crossovers of the respiratory gas flow curve are shifted whereby the synchronization with the respiratory gas efforts of the patient is affected.

The drop of the respiratory gas flow to 25% of the maximum value can be used as a switchover criterion. However, if this switchover criterion is used, for example, in an assisted ventilation and there is large leakage present, then the switchover is not triggered when the leakage lies above this 25%, limit. For this case, it is known to input a maximal inspiration time as an additional switchover criterion in accordance with which a switchover to the expiration takes place in each case. A criterion of this kind is disclosed, for example, in the German publication entitled "Gebrauchsanweisung Evita Intensivpflege-Ventilator", pages 82 and 83 (June 1991), and published by Drägerwerk Aktiengesellschaft of Germany.

The leakage flow is generally not constant and is, however, dependent upon respiratory gas pressure in each case. For this reason, no satisfactory criteria for the switchover of the respiratory phases can be obtained only from the trigger thresholds obtained from the respiratory gas flow curve or additional time inputs.

U.S. Pat. No. 3,903,881 discloses a ventilating system wherein the leakage at the lower pressure level is compensated by a compensating flow. The next inspiration stroke is triggered when the inspiration flow exceeds an adjusted trigger threshold. The trigger threshold must then be so adjusted that it lies just above the compensating flow. The trigger threshold must be adjusted for each change of the respiratory gas pressures because the leakage flow is influenced by the ventilating pressure. For a trigger threshold which is set too low, the next inspiration stroke is triggered too soon. On the other hand, the system becomes insensitive when the trigger threshold is set too high and the trigger threshold is only exceeded with the first forceful inhalation.

SUMMARY OF THE INVENTION

It is an object of the invention to improve a ventilating system of the kind described above so that a good adaptation of the ventilating system to the breathing effort of the patient is provided even when leakages are present.

The ventilating system of the invention is for supplying a patient with respiratory gas during inspiratory and expiratory phases of breathing. The ventilating system includes: a pressure measuring device for measuring a first curve representing respiratory gas pressure; a flow measuring device for measuring a second curve representing respiratory gas flow; valve means for providing predetermined pressures of the respiratory gas during the inspiratory and expiratory phases; an evaluation circuit for processing the curves and for controlling the valve means to switch over between the phases in dependence upon predetermined trigger thresholds $T_{IL}$ and $T_{EL}$ of the second curve; and, the evaluation circuit including means for executing a logic operation pursuant to a predetermined function between the first and second curves during the inspiratory and expiratory phases to form an inspiratory ancillary trigger threshold $Z_I$ and an expiratory ancillary trigger threshold $Z_E$ and to add the ancillary trigger thresholds ($Z_I$ and $Z_E$) to the inspiratory and expiratory thresholds ($T_{IL}$ and $T_{EL}$), respectively, to form composite trigger thresholds ($T_{IL}+Z_I$) and ($T_{EL}+Z_E$) for controlling the switchover between the phases.

The method of the invention is for triggering breathing phases in a ventilating system for supplying a patient with respiratory gas during inspiratory and expiratory phases of breathing. The method includes the steps of: adjusting an inspiratory pressure $P_I$ during an inspiratory phase and adjusting an expiratory pressure $P_E$ during an expiratory phase; measuring a first curve representing respiratory gas pressure; measuring a second curve representing respiratory gas flow; providing predetermined trigger thresholds $T_{IL}$ and $T_{EL}$ of the second curve for use in forming switchover values for switching over between the phases; determining a volume $V_{MI}$ of respiratory gas averaged over the inspiratory phase and a volume $V_{ME}$ of respiratory gas averaged over the expiratory phase; determining the mean values of the inspiratory pressure $P_I$ and the expiratory pressure $P_E$; forming an inspiratory ancillary trigger threshold $Z_I$ from at least the product of the mean expiratory pressure $P_E$ and the difference ($V_{MI}-V_{ME}$); forming an expiratory ancillary trigger threshold $Z_E$ from at least the product of the mean inspiratory pressure $P_I$ and the difference ($V_{MI}-V_{ME}$); switching from the inspiratory phase to the expiratory phase in response to a drop of the second curve to a composite trigger threshold ($T_{EL}+Z_E$); and, switching from the expiratory phase to the inspiratory phase in response to an increase of the second curve to a composite trigger threshold ($T_{IL}+Z_I$).

The advantage of the invention is seen essentially in that the switchover values are dynamically adapted to the compensating flow metered for compensating a leakage caused either by the patient or by the system. This adaptation is provided in that an additional criterion in the form of an inspiration trigger ancillary threshold $Z_I$ and an expiration trigger ancillary threshold $Z_E$ is obtained by logically coupling the respiratory gas flow to the respiratory gas pressure. With this criterion, an adaptation of the respiratory phase switchover time points of a system having leakage to the switchover time points of a leakage-free system is possible. The magnitude and the time-dependent trace of the leakage flow do not have to be known.

The coupling between the respiratory gas flow and the respiratory gas pressure advantageously have the following form:

$$Z_I = \frac{P_E}{P_I + P_E} (V_{MI} - V_{ME}) \text{ and}$$

$$Z_E = \frac{P_I}{P_I + P_E} (V_{MI} - V_{ME})$$

wherein: $V_{MI}$ is the value of the respiratory gas flow V averaged over the inspiration; $V_{ME}$ is the value of the respiratory gas flow V averaged over the expiration. The respiratory pressure $P_I$ is the averaged respiratory pressure during the inspiration and $P_E$ is the averaged respiratory pressure during the expiration. The new trigger thresholds are $T_{EL}$ plus $Z_E$ and $T_{IL}$ plus $Z_I$.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
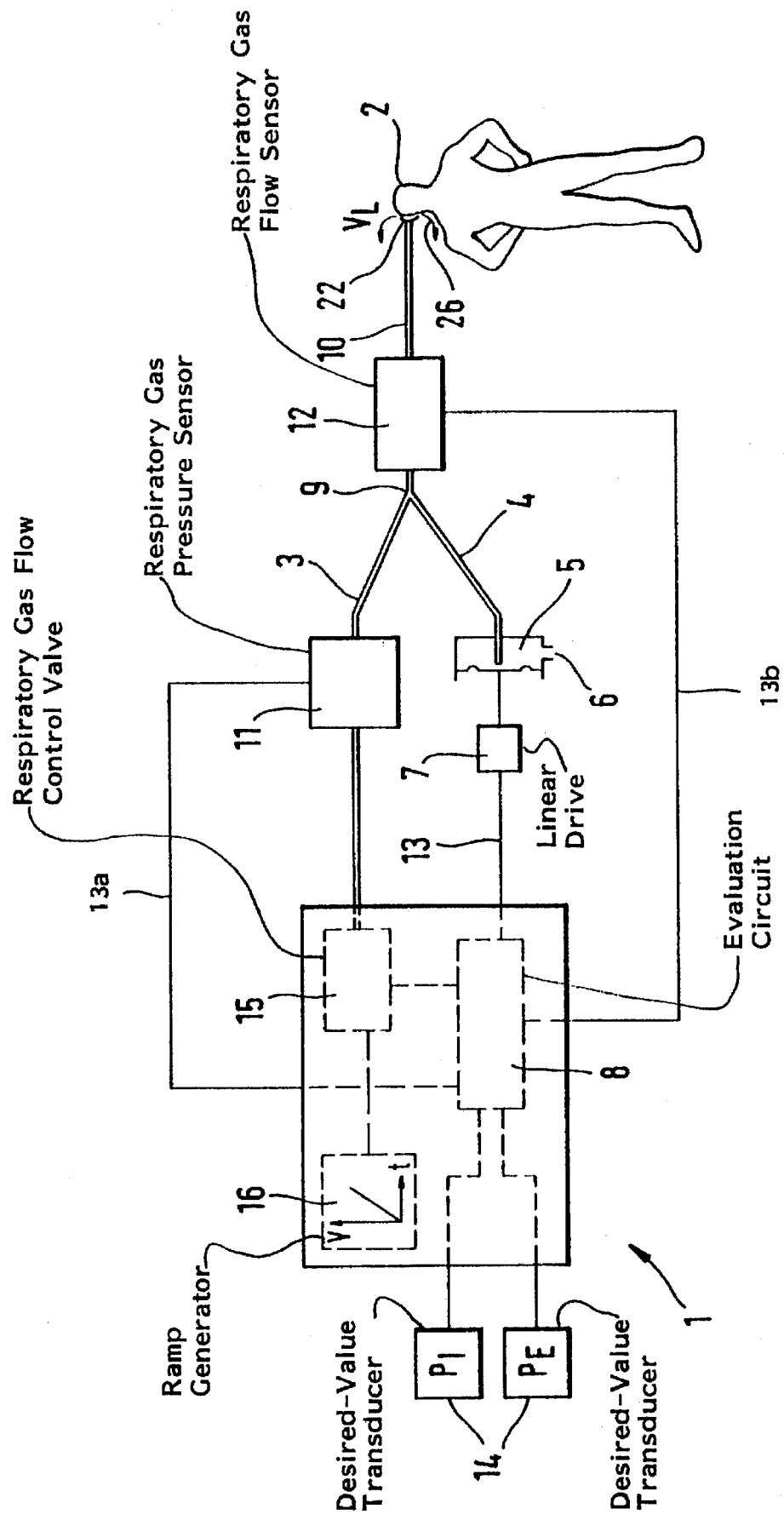
FIG. 1 is a ventilating system according to an embodiment of the invention.

FIG. 1 shows a ventilating system 1 for supplying a patient 2 with respiratory gas via an inspiration line 3 and for discharging the exhaled gas via an expiration line 4 and a PEEP valve 5 leading to an expiration outlet 6. The PEEP valve 5 adjusts an expiration pressure $P_E$ on the patient during the expiration. The PEEP valve 5 is driven by a linear drive 7 which is connected via a signal line 13 to an evaluation circuit 8 of the ventilating system 1. The inspiration line 3 and the expiration line 4 come together in a Y-piece 9 from which a common respiratory gas line 10 leads to the patient 2. The respiratory gas line 10 conducts respiratory gases for both inspiration and expiration in common.

A respiratory gas pressure sensor 11 is connected into the inspiratory line 3 to measure the respiratory gas pressure P and a respiratory gas flow sensor 12 is mounted in the respiratory gas line 10 to measure the respiratory gas flow V. The sensors (11, 12) are connected via signal lines 13a and 13b, respectively, to the evaluation circuit 8. In this connection, the respiratory gas flow V is understood to be the time-dependent discharge of the respiratory gas volume, that is, the volume per unit of time.

The evaluation circuit 8 includes a microprocessor (not shown) which functions as a central control unit of the ventilating system 1. The microprocessor stores and evaluates the respiratory gas pressure signals supplied by sensor 11 and the respiratory gas flow signals supplied by sensor 12. The microprocessor also controls the respiratory phases and controls the respiratory gas flow control valve 15 for supplying the patient 2 with respiratory gas. A desired-value transducer 14 is connected to the evaluation circuit 8 for supplying the inspiratory pressure $P_I$ and the expiratory pressure $P_E$. The desired-value transducer 14 can be adjusted to preselected values of $P_I$ and $P_E$ by the operator.

The respiratory gas flow V to the patient 2 is metered via the respiratory gas flow control valve 15 which is connected to a pressure gas source 30. During inspiration, the respiratory gas flow control valve 15 receives input values from a ramp generator 16 in such a manner that, during inspiration, a pregiven inspiratory pressure $P_I$ is present and, during expiration, and together with the PEEP valve 5, a pregiven expiratory pressure $P_E$ is provided.

Figure 2:
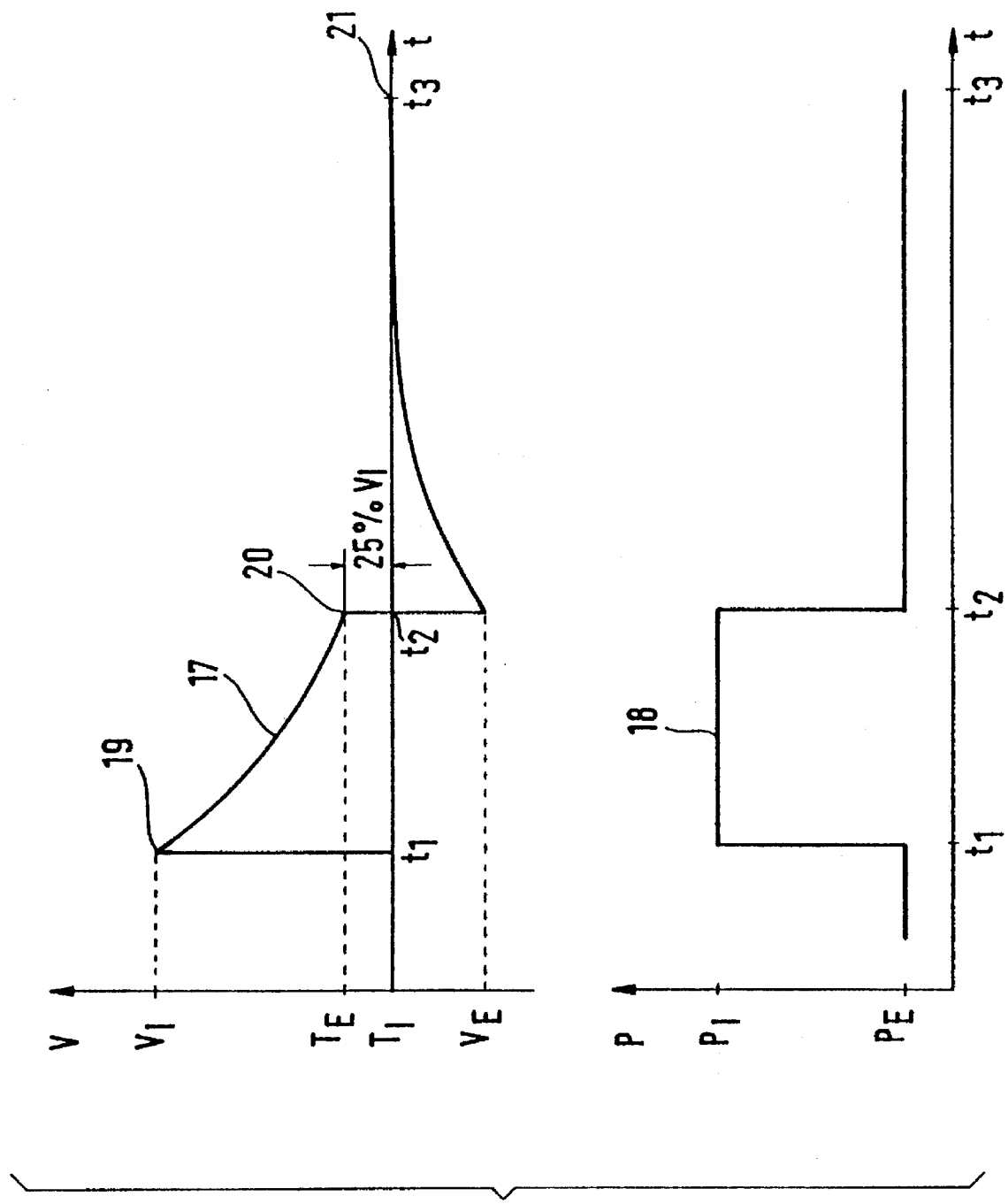
FIG. 2 shows a graph of respiratory gas flow (V) as a function of time (t) and a graph of respiratory gas pressure (P) as a function of time (t) both for the ventilating system of FIG. 1; and, FIG. 3 shows a graph of the respiratory gas flow and a graph of the respiratory gas pressure of the ventilating system of FIG. 1 when there is leakage.

The respiratory gas flow V and the respiratory gas pressure P are represented graphically in FIG. 2 as functions of time (t). Thus, reference numeral 17 identifies the respiratory gas flow curve and reference numeral 18 identifies the respiratory gas pressure curve. The curves 17 and 18 are presented in ideal form, that is, the respiratory gas flow V reaches the maximum inspiration flow $V_I$ as maximum value in a very short time and the respiratory gas pressure P increases to the inspiratory gas pressure $P_I$ at time point $t_1$ likewise in a short time.

From curve 17, it can be seen that the respiratory gas flow V becomes decreasingly and continuously less between the points (19, 20), that is, between time point $t_1$ and $t_2$, in dependence upon the fill level of the lungs of the patient 2. The respiratory gas flow V has dropped to 25% of the maximum inspiratory flow $V_I$ at point 20. The time point 20 is an expiratory trigger threshold $T_E$ and is the time point at which the switchover from the inspiratory phase to the expiratory phase takes place. The expiratory trigger threshold $T_E$ is stored in the evaluation circuit 8.

At the start of the expiratory phase (that is, starting at time point $t_2$, namely, point 20), the sign of the curve 17 reverses and the respiratory gas flow V reduces continuously from a maximum expiratory flow $V_E$ down to zero at time point $t_3$ (at point 21). The zero crossover of the respiratory gas flow V is an inspiratory trigger threshold $T_I$ which is likewise stored in the evaluation circuit 8 and operates to initiate a new inspiratory stroke. In the embodiment described above, the time interval between $t_2$ and $t_3$ is approximately twice as long as the time interval between $t_1$ and $t_2$ so that the breathing time ratio between inspiration and expiration is approximately 1:2.

The curves (17, 18) shown in FIG. 2 refer to a so-called tight ventilating system 1, that is, without leakage so that the leakage flow $V_L$ is zero. In a real ventilating system 1, leakages as a rule do occur. These leakages can be caused, for example, by a mask 22 which is not seated tightly on the face of the patient 2 or by fistulas in the patient's lungs. If, for example, a leakage flow $V_L$ flows in the direction of arrows 26 because of the loose mask 22 into the ambient, then, if the same inspiratory and expiratory pressures $P_I$ and $P_E$ are to be reached, a higher maximum inspiratory flow $V_{IL}$ is needed during the inspiration and, during expiration, additional respiratory gas must be metered into the inspiratory line 3 in order to maintain the expiratory pressure $P_E$ constant. Contributing to the difficulty in this situation is that the leakage flow $V_L$ is generally dependent upon pressure, that is, $V_L$ is greater during inspiration than during the expiration. The letter "L" refers here to the ventilating system 1 with leakage.

Figure 3:
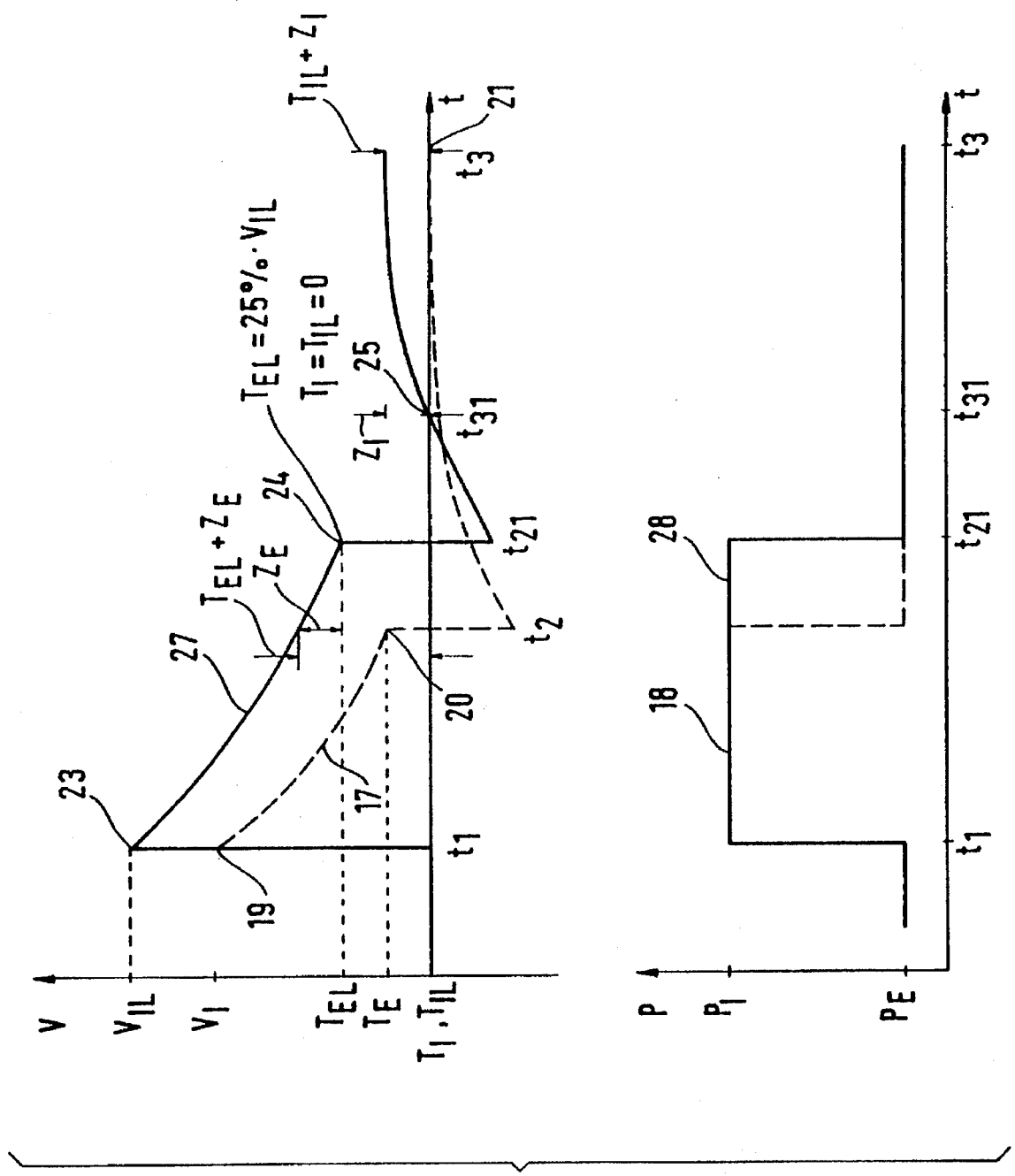

FIG. 3 shows, as an example, a respiratory gas flow curve 27 and a respiratory gas pressure curve 28 for a ventilating system 1 wherein leakage is present. For a better overview, the curves 17 and 18 of FIG. 2 are shown in FIG. 3 in phantom outline.

Because of the leakage flow $V_L$, the respiratory gas flow curve 27 now increases to the maximum value $V_{IL}$ (point 23) and then drops continuously to point 24. The expiratory trigger threshold $T_{EL}$ is reached when the respiratory gas flow has dropped to 25% of the maximum value $V_{IL}$, that is, at point 24. A switchover to the expiratory phase takes place at point 24. Since the leakage flow $V_L$ is likewise present during expiration, additional expiratory gas must be metered into the inspiratory line 3 via the respiratory gas flow control valve 15 in order to maintain the constant expiratory pressure $P_E$. Because of this metering of respiratory gas, the respiratory gas flow curve 27 does not approach the abscissa asymptotically as does the curve 17; instead, the respiratory gas flow curve 27 intersects the abscissa at point 25 and thereafter assumes a positive sign.

Since the zero crossover of the respiratory gas flow V is stored in the evaluation circuit 8 as the inspiratory trigger threshold $T_{IL}$ also for the ventilating system 1 subjected to leakage, the ventilating system 1 would execute a new inspiratory stroke at time point $t_{31}$ (point 25). This new inspiratory stroke is not shown in FIG. 3 so that a better overview is provided.

$T_I$ and $T_{IL}$ are numerically the same in the above-described case because the trigger criterion is the zero crossover of the respiratory gas flow. They are, however, different when the trigger criterion is, for example, referred to a specific percentage component of a respiratory gas flow. If the respiratory gas pressure curve with leakage 28 is compared to the respiratory gas pressure curve without leakage 18, then, for a ventilating system 1 with leakage and the trigger thresholds $T_{IL}$ and $T_{EL}$ in accordance with the state of the art, the inspiratory time is lengthened, that is, the patient inhales too long and the expiratory time is shortened and the patient receives the next inhalation stroke during the expiratory phase even without spontaneous breathing. For a better overview, the inspiratory stroke is not shown in the respiratory gas pressure curve 28 which would otherwise start at time point $t_{31}$.

The invention now provides that the trigger thresholds $T_{IL}$ and $T_{EL}$ are corrected by including trigger ancillary thresholds $Z_I$ and $Z_E$ in such a manner that the switchover of the respiratory phases takes place at the time points $t_1$, $t_2$ and $t_3$, points (19, 20, 21) as with a leakage-free ventilating system 1.

The inspiratory trigger ancillary threshold $Z_I$ and the expiratory trigger ancillary threshold $Z_E$ can be derived from a functional relationship between the respiratory gas pressure P and the leakage flow $V_L$. This functional relationship can be a linear dependency between the respiratory gas pressure P and the leakage flow $V_L$ as it is present in a laminar flow or the root of the leakage flow $V_L$ is proportional to the respiratory gas pressure P as, for example, for a turbulent flow.

Since the leakage flow $V_L$ cannot be measured directly, a mean value of the respiratory gas flow V is computed in the evaluation circuit 8 as $V_{MI}$ and $V_{ME}$ during inspiration as well as during expiration and the mean respiratory gas pressures $P_I$ and $P_E$ are measured.

For the exception of a laminar leakage flow $V_L$, the trigger ancillary thresholds $Z_I$ and $Z_E$ result as follows:

$$Z_I = \frac{P_E}{P_I + P_E} (V_{MI} - V_{ME})$$

$$Z_E = \frac{P_I}{P_I + P_E} (V_{MI} - V_{ME})$$

The switchover between the inspiratory phase and the expiratory phase and vice versa takes place, in a ventilating system 1 having leakage, at the trigger thresholds $T_{EL}$ plus $Z_E$ and $T_{IL}$ plus $Z_I$. The mean inspiratory volume $V_{MI}$ is approximately equal to the expiratory volume $V_{ME}$ for a leakage-free ventilating system 1. For this reason, $Z_I$ and $Z_E$ are zero for this case.

It is understood that the foregoing description is that of the preferred embodiments of the invention and that various changes and modifications may be made thereto without departing from the spirit and scope of the invention as defined in the appended claims.

What is claimed is:

1. A ventilating system for supplying a patient with respiratory gas during inspiratory and expiratory phases of breathing, the ventilating system comprising:

a source of compressed respiratory gas;

valve means connected to said source of compressed respiratory gas and being provided for metering a flow of said respiratory gas to the patient thereby adjusting predetermined pressures of said respiratory gas during said inspiratory phases and expiratory phases of the patient;

a pressure measuring device for measuring the pressure of the respiratory gas supplied to the patient during inspiration and expiration and for providing measured pressure values defining a first curve representing respiratory gas pressure;

a flow measuring device for measuring respiratory gas flow during inspiration and expiration and for providing measured flow values defining a second curve representing respiratory gas flow and said second curve having an amplitude;

an evaluation circuit for processing said curves and for controlling said valve means to switch over between said inspiratory and expiratory phases of the patient upon predetermined values of the amplitude of said second curve, said predetermined values being trigger thresholds $T_{IL}$ and $T_{EL}$ of said second curve; and, said evaluation circuit including means for executing a logic operation pursuant to a predetermined function between said first and second curves during said inspiratory phases and expiratory phases of the patient to form an inspiratory ancillary trigger threshold $Z_I$ and an expiratory ancillary trigger threshold $Z_E$ and to add said ancillary trigger thresholds ($Z_I$ and $Z_E$) to said inspiratory and expiratory thresholds ($T_{IL}$ and $T_{EL}$), respectively, to form composite trigger thresholds ($T_{IL}+Z_I$) and ($T_{EL}+Z_E$) for controlling the switchover between said phases.

2. The ventilating system of claim 1, wherein said means for executing said logic operation is configured to compute said ancillary trigger thresholds ($Z_I$ and $Z_E$) as follows:

$$Z_I = \frac{P_E}{P_I + P_E} (V_{MI} - V_{ME})$$

$$Z_E = \frac{P_I}{P_I + P_E} (V_{MI} - V_{ME})$$

wherein:

$V_{MI}$=the value of the respiratory gas flow v averaged over the inspiratory phase;

$V_{ME}$=the value of the respiratory gas flow averaged over the expiratory phase;

$P_I$=the mean respiratory gas pressure during the inspiratory phase;

$P_E$=the mean respiratory gas pressure during the expiratory phase;

$T_{EL}+Z_E$=a first new trigger threshold; and, $T_{IL}+Z_I$=a second new trigger threshold.

3. A method of triggering breathing phases in a ventilating system for supplying a patient with respiratory gas from a source of compressed respiratory gas during inspiratory and expiratory phases of breathing, the method comprising the steps of:

adjusting an inspiratory pressure $P_I$ during an inspiratory phase and adjusting an expiratory pressure $P_E$ during an expiratory phase;

measuring the pressure of the respiratory gas supplied to the patient during inspiration and expiration and providing measured pressure values defining a first curve representing respiratory gas pressure;

measuring respiratory gas flow during inspiration and expiration and providing measured flow values defining a second curve representing respiratory gas flow and said second curve having an amplitude;

utilizing an evaluation circuit to process said curves and controlling a valve to switch over between said inspiratory and expiratory phases of the patient upon predetermined values of the amplitude of said second curve, said predetermined values being trigger thresholds $T_{IL}$ and $T_{EL}$ of said second curve;

determining a volume $V_{MI}$ of respiratory gas averaged over the inspiratory phase and a volume $V_{ME}$ of respiratory gas averaged over the expiratory phase;

determining the mean values of said inspiratory pressure $P_I$ and said expiratory pressure $P_E$;

forming an inspiratory ancillary trigger threshold $Z_I$ from at least the product of said mean expiratory pressure $P_E$ and the difference $(V_{MI}-V_{ME})$;

forming an expiratory ancillary trigger threshold $Z_E$ from at least the product of said mean inspiratory pressure $P_I$ and the difference $(V_{MI}-V_{ME})$;

switching from the inspiratory phase to the expiratory phase in response to a drop of said second curve to a composite trigger threshold $(T_{EL}+Z_E)$; and, switching from the expiratory phase to the inspiratory phase in response to an increase of said second curve to a composite trigger threshold $(T_{IL}+Z_I)$.

4. The method of claim 3, wherein said ancillary trigger thresholds $Z_I$ and $Z_E$ are computed from the equations:

$$Z_I = \frac{P_E}{P_I + P_E} (V_{MI} - V_{ME})$$

$$Z_E = \frac{P_I}{P_I + P_E} (V_{MI} - V_{ME}).$$

* * * * *